United States Patent
Toumazou et al.

(10) Patent No.: US 10,811,140 B2
(45) Date of Patent: Oct. 20, 2020

(54) SECURE SET-UP OF GENETIC RELATED USER ACCOUNT

(71) Applicant: DNANUDGE LIMITED, London (GB)

(72) Inventors: Christofer Toumazou, London (GB); Tsz-Kin Hon, London (GB)

(73) Assignee: DNANUDGE LIMITED, London (GB)

(*) Notice: Subject to any disclaimer, the term of this patent is extended or adjusted under 35 U.S.C. 154(b) by 0 days.

(21) Appl. No.: 16/357,982

(22) Filed: Mar. 19, 2019

(65) Prior Publication Data

US 2020/0303076 A1  Sep. 24, 2020

(51) Int. Cl.
| | | |
|---|---|---|
| *G16H 50/30* | (2018.01) | |
| *G16H 80/00* | (2018.01) | |
| *G06Q 30/06* | (2012.01) | |
| *G06F 21/62* | (2013.01) | |
| *G06F 21/31* | (2013.01) | |

(Continued)

(52) U.S. Cl.
CPC ............. *G16H 50/30* (2018.01); *G06F 1/163* (2013.01); *G06F 21/31* (2013.01); *G06F 21/6245* (2013.01); *G06K 19/06028* (2013.01); *G06Q 30/0631* (2013.01); *G16H 80/00* (2018.01)

(58) Field of Classification Search
CPC ........ G16H 10/60; G16H 10/40; G16H 50/30; G16H 80/00; G06Q 50/24; G06F 19/3418
See application file for complete search history.

(56) References Cited

U.S. PATENT DOCUMENTS

| | | |
|---|---|---|
| 2,416,269 A | 2/1947 | Paul |
| 3,885,383 A | 5/1975 | Tanaka |
| 5,284,753 A | 2/1994 | Goodwin |

(Continued)

FOREIGN PATENT DOCUMENTS

| | | |
|---|---|---|
| DE | 3508366 A1 | 12/1985 |
| EP | 0576998 A1 | 1/1994 |

(Continued)

OTHER PUBLICATIONS

Andrianova,M et al.,Amplified Detection of the Aptamer-Vanillin Complex with the Use of Bsm DNA Polymerase, Sensors, 18, 49 available at www.mdpi.com/1424-8220/1811/49 ,2018 ,1-13.

(Continued)

*Primary Examiner* — Jonathan Durant
(74) *Attorney, Agent, or Firm* — Saul Ewing Arnstein & Lehr LLP

(57) ABSTRACT

A method of setting up a wearable user device to allow a user to scan products and obtain product recommendations based on the user's personal biological/genetic data, using a cartridge to perform a test on the user's personal biological/genetic data via a desktop test control system into which the cartridge is plugged. A user account is associated with a cartridge ID read from the cartridge. The cartridge ID is also read using the wearable user device and passed to the server when the wearable user device is coupled to the test control system, associating the test with the user account. The test control system communicates test results to the server which analyses the test results to generate analysis results. The analysis results are then downloaded to the wearable user device. Product codes are also downloaded to the wearable user device, and stored in association with the product codes.

19 Claims, 3 Drawing Sheets

(51) Int. Cl.
  *G06F 1/16*   (2006.01)
  *G06K 19/06*  (2006.01)

(56) References Cited

U.S. PATENT DOCUMENTS

| | | |
|---|---|---|
| 5,478,989 A | 12/1995 | Shepley |
| 5,935,858 A | 8/1999 | Herst |
| 6,025,281 A | 2/2000 | Passlack et al. |
| 6,587,022 B1 | 7/2003 | Devine |
| 6,652,455 B1 | 11/2003 | Kocher |
| 6,711,414 B1 | 3/2004 | Lightman |
| 6,980,999 B1 | 12/2005 | Grana |
| 7,805,319 B2 | 9/2010 | Badinelli |
| 7,851,207 B1 | 12/2010 | Sagripanti |
| 8,386,519 B2 | 2/2013 | Kenedy et al. |
| 8,630,448 B1 | 1/2014 | Shanmugam et al. |
| 9,013,300 B2 | 4/2015 | Felix |
| 9,414,623 B2 | 8/2016 | Minvielle |
| 9,724,023 B2 | 8/2017 | Swenson |
| 9,775,015 B1 | 9/2017 | Mishra et al. |
| 9,858,799 B1 | 1/2018 | Deluca et al. |
| 9,900,061 B1 | 2/2018 | Lui et al. |
| 9,901,301 B2 | 2/2018 | Brenner et al. |
| 2001/0051377 A1 | 12/2001 | Hammer et al. |
| 2003/0005967 A1 | 1/2003 | Karp |
| 2003/0134679 A1 | 7/2003 | Siegel et al. |
| 2003/0162304 A1 | 8/2003 | Dority et al. |
| 2003/0208110 A1 | 11/2003 | Mault et al. |
| 2003/0226695 A1 | 12/2003 | Mault |
| 2003/0230606 A1 | 12/2003 | Devinie |
| 2004/0018523 A1 | 1/2004 | Hawkins |
| 2004/0103033 A1 | 5/2004 | Reade et al. |
| 2004/0143447 A1 | 7/2004 | Lay |
| 2005/0021679 A1 | 1/2005 | Lightman et al. |
| 2006/0256074 A1 | 11/2006 | Krum et al. |
| 2008/0208971 A1 | 8/2008 | Costin et al. |
| 2008/0263011 A1 | 10/2008 | Badinelli |
| 2010/0113892 A1 | 5/2010 | Kaput et al. |
| 2010/0169340 A1 | 7/2010 | Kenedy et al. |
| 2010/0312668 A1 | 12/2010 | Notsani |
| 2011/0166881 A1 | 7/2011 | Brazzo et al. |
| 2011/0220502 A1 | 9/2011 | Selden et al. |
| 2011/0318717 A1 | 12/2011 | Adamowicz |
| 2012/0005098 A1* | 1/2012 | Gross ............... G06F 21/31 705/50 |
| 2012/0010897 A1 | 1/2012 | Bagan |
| 2012/0046767 A1 | 2/2012 | Shimohata et al. |
| 2012/0214159 A1* | 8/2012 | George ............ G01N 35/00603 435/6.11 |
| 2013/0023058 A1 | 1/2013 | Toumazou et al. |
| 2013/0096943 A1* | 4/2013 | Carey ................ G06Q 10/10 705/2 |
| 2013/0137169 A1 | 5/2013 | Kojima |
| 2013/0262298 A1 | 10/2013 | Morley |
| 2013/0268292 A1 | 10/2013 | Kim et al. |
| 2013/0275318 A1 | 10/2013 | Minvielle |
| 2013/0337974 A1 | 12/2013 | Yanev et al. |
| 2014/0085077 A1 | 3/2014 | Luna et al. |
| 2014/0090039 A1 | 3/2014 | Brow |
| 2014/0107932 A1 | 4/2014 | Luna |
| 2014/0156295 A1 | 6/2014 | Cooper |
| 2014/0214623 A1 | 7/2014 | Cancro et al. |
| 2014/0277649 A1 | 9/2014 | Chong et al. |
| 2014/0335490 A1 | 11/2014 | Baarman et al. |
| 2015/0044758 A1 | 2/2015 | Amshey et al. |
| 2015/0073907 A1 | 3/2015 | Purves et al. |
| 2015/0087478 A1 | 3/2015 | Zhang et al. |
| 2015/0100445 A1 | 4/2015 | Johnson et al. |
| 2015/0112857 A1 | 4/2015 | Gellis et al. |
| 2015/0170249 A1 | 6/2015 | Cockcroft |
| 2015/0227890 A1 | 8/2015 | Bednarek et al. |
| 2015/0242837 A1 | 8/2015 | Yarbrough et al. |
| 2015/0251074 A1 | 9/2015 | Ahmed et al. |
| 2015/0317503 A1 | 11/2015 | Powell et al. |
| 2015/0331946 A1* | 11/2015 | Balwani ............. G16H 10/40 707/769 |
| 2016/0004891 A1 | 1/2016 | Moon et al. |
| 2016/0071423 A1 | 3/2016 | Sales et al. |
| 2016/0219124 A1 | 7/2016 | Elgrichi |
| 2017/0061200 A1 | 3/2017 | Wexler et al. |
| 2017/0098268 A1* | 4/2017 | Karvela ............. G16B 50/00 |
| 2017/0166848 A1* | 6/2017 | Toumazou ........... C12Q 1/6874 |
| 2017/0242963 A1 | 8/2017 | Cohen et al. |
| 2017/0323057 A1 | 11/2017 | Karvela et al. |
| 2017/0345279 A1 | 11/2017 | Abraham et al. |
| 2018/0053242 A1 | 2/2018 | Agrawal |
| 2018/0095429 A1 | 4/2018 | Weinstein et al. |
| 2018/0140203 A1 | 5/2018 | Wang et al. |
| 2018/0144101 A1 | 5/2018 | Bitran et al. |
| 2018/0182253 A1 | 6/2018 | Hor-Lao et al. |
| 2018/0236242 A1 | 8/2018 | Balinski et al. |
| 2018/0263539 A1 | 9/2018 | Javey et al. |
| 2018/0374567 A1 | 12/2018 | Toumazou et al. |

FOREIGN PATENT DOCUMENTS

| | | |
|---|---|---|
| EP | 1329835 A1 | 7/2003 |
| EP | 2416269 A2 | 2/2012 |
| EP | 2733579 A2 | 1/2019 |
| GB | 2509481 A | 7/2014 |
| JP | 2002056278 A | 2/2002 |
| JP | 2002366888 A | 12/2002 |
| JP | 2005157985 A | 6/2005 |
| JP | 2013191048 A | 9/2013 |
| JP | 2014525094 A | 9/2014 |
| WO | 01/13317 A2 | 2/2001 |
| WO | 02063415 A2 | 8/2002 |
| WO | 03027236 A2 | 4/2003 |
| WO | 03105445 | 12/2003 |
| WO | 2005027716 A2 | 3/2005 |
| WO | 2008019695 A2 | 2/2008 |
| WO | 2008107014 A1 | 9/2008 |
| WO | 2012/135557 | 10/2012 |
| WO | 2013008042 A1 | 1/2013 |
| WO | 2013010685 A1 | 1/2013 |
| WO | 2014008381 A2 | 1/2014 |
| WO | 2014022907 A1 | 2/2014 |
| WO | 2015050174 A1 | 4/2015 |
| WO | 2015054034 A1 | 4/2015 |
| WO | 2015/077512 | 5/2015 |
| WO | 2016019476 A1 | 2/2016 |
| WO | 2016117726 A1 | 7/2016 |
| WO | 2016170445 A2 | 10/2016 |
| WO | 2017055867 A1 | 4/2017 |

OTHER PUBLICATIONS

Guo,X et al.,Development of an Ultrasensitive Aptrasensor for the Detection of Aflatoxin B1, Biosensors Bioelectornics, vol. 56 ,2014 ,340-344.

Li,F. et al.,Aptamers Facilitating Amplified Detection of Biomolecules, Analytical CHemistra, vol. 87 ,2015 ,274-292.

Ma, et al.,Femtogram Ultrasensitive Aptasensor for the Detection of Ochratoxin A, Biosensors & Bioelectronics, vol. 42 ,2013 ,545-549.

Spurgeon,Sandra et al.,High Throughput Gene Expression Measurement with Real Time PCR in a Microfluidic Dynamic Array, PLoS One, vol. 3, Issue 2, e1662 ,Feb. 2008 ,1-7.

Retrieved from the Internet: URL:https://www.youtube.com/watch?v=13m62ZgeY6U [retrieved on Feb. 8, 2019 XP054979164, May 30, 2015.

Anonymous , "Codecheck Barcode and QR Scan: Gesunder Scanner", Retrieved from the Internet: URL:https://www.androidpit.de/codecheck-barcode-qr-scan-gesunder-scanner [retrieved on Feb. 7, 2019] XP002788879, Dec. 24, 2016.

Eng, Donna S., et al., "The Promise and Peril of Mobile Health Applications for Diabetes and Endocrinology: Mobile health applications in diabetes and endocrinology", Pediatric Diabetes, vol. 14, No. 4, pp. 231-238 XP055553599, Apr. 30, 2013.

* cited by examiner

SECURE SET-UP OF GENETIC RELATED USER ACCOUNT

TECHNICAL FIELD OF THE INVENTION

The present invention relates to the secure set-up of a user account associated with genetic-related data and in particular where the set-up involves the transfer of genetic-related data to a user wearable device.

BACKGROUND OF THE INVENTION

Semiconductor nanotechnology and optical technologies have made significant contributions to people's lifestyle, especially by facilitating hardware miniaturisation. Its application to the sequencing and genotyping industry has enabled so-called "lab-on-chip" systems. Depending on the biological questions/genes of interest, primer(s)/probe(s)—more generally referred to as "biomarkers"—can be designed accordingly. A biomarker is an oligonucleotide such as a DNA molecule and may target certain gene(s)/variation(s). A biomarker may alternatively, for example, be an antibody or an antigen. By applying/choosing different types of biomarkers on such systems, an individual can test his/her biological sample, DNA, RNA, protein etc., (extracted locally or remotely by a third party from e.g. saliva, blood, urine, tissue, stool, hair etc.) for specific traits, possibly as dictated by certain lifestyle concerns or interest.

Such "personal" genetic or biological information enables medical decisions to be made more effectively, for example, by selecting treatments or drug doses which are more likely to work for particular patients. Identifying individual differences at a molecular level also allows lifestyle and dietary/nutritional advice to be tailored according to the needs of individuals or particular classes of individuals. A number of private companies have been established in order to cater for the growing consumer genetics market and every day new genetic traits are being identified and described, generating a continuously expanding catalogue of biomarkers that have the potential to offer insight into the health, wellbeing, and, in the case of genetic variations, phenotype, of a great many people.

Typically, when an individual that wants to gain access to information related to his/her genetics or health condition, whether for a specific purpose/concern or for general interest, he or she needs to go through a private clinic or professional body, provide sample to central labs (either in person or by post). Such a process is time consuming, inconvenient and may invade the individual's privacy. For example, many tests are based on blood analysis, which requires the individual to attend a sample collection session with an expert. In the most convenient available approach, he/she needs to order a kit for collecting saliva sample and then post it to the lab having obtained the sample themselves.

User privacy is of critical importance when it comes to offering personalised genetic-based services, not only because of the real threat of data leaking to unscrupulous parties, but also because of the need to ensure that users trust the services and are therefore willing to make use of them. Conventional personalised genetic-based services such as that offered by 23andme™ rely on users sending samples of their genetic material to a remote facility where analysis is performed and the results interpreted, before the results are returned to the users. Despite privacy safeguards, users are wary of such services as the results and analysis are to a large extent beyond their control.

The majority of the currently available genetic services offer wide genome screening; e.g., using a predefined platform tagged with more than 100,000 biomarkers and screening irrespectively all client samples for all genetic biomarkers. This means that a high proportion of customers are being screened by default for genetic traits that they may not want to know about; for instance, an individual purchasing a test in order to determine his/her predisposition to detoxification will be also screened for serious neurodegenerative diseases such as Alzheimer's and Parkinson's disease. Giving a customer access to information related to concerns that the customer did not initially have, may have a detrimental effect on his or her socio/psychological balance.

Confidentiality concerns may not be solely related to genetic results, i.e. what genetic variants the customer carries, but also relate to the personal concerns that motivated the customer to consider having a genetic test, for instance predisposition to impotence, baldness, drug addiction, alcoholism etc. If this information were to become available to health insurance providers, potential employers etc, an individual could be "genetically stigmatised" and "classified". The impact of such disclosures on an individual's life could be enormous.

US2017/0323057A1 describes a wearable device for providing product recommendations, for example food and drink products, based on a user's genetic data. The wearable device incorporates a laser scanner or barcode reader which the wearer of the device uses to identify a product he or she is interested in purchasing or consuming. The device then provides an indication whether or not the product is recommended for the wearer based on his or her genetics.

US2017/0098268 describes a device for processing biological samples which is suitable for use in a non-technical environment such as a retail premise. A user provides a genetic sample, e.g. using a buccal swab, which is then applied to a test cartridge to identify whether a particular biomarker is present in the user's genetic material, e.g. by carrying out Single Nucleotide Polymorphism (SNP) genotyping of the sample. As will be well known to the person of skill in the art, SNP genotyping involves detecting which of a number of genetic variations is present at each of one or more SNPs of a person or animal's genome. These SNP variations can provide markers to a condition or trait of the person or animal whose genome is being analysed.

Although there are considerable benefits with providing easy access for users to genetic or biological testing facilities, it is important that processes and systems are developed which ensure that user confidentiality is respected. In particular, performing personally sensitive tests in a busy, public place such as a retail environment may lead to mistakes or even malicious activities which deprive users of their right to privacy.

SUMMARY OF THE INVENTION

The approach proposed here address confidentiality and user confidence concerns, vis-à-vis a wearable computer device that stores biologically/genetically derived data, by providing test cartridges with unique computer readable cartridge identifiers. This ID read by two separate means: firstly by a computer device that is used to set up a user account on some server system, and secondly by the wearable computer device itself. Prior to or during the test, the wearable computer device communicates the read ID to server system so that the test, and its results, can be unambiguously associated with the user account.

According to a first aspect of the present invention there is provided a method of installing, into a memory of a wearable computer device, results obtained by analysing a biological sample of a user. The method comprises: providing a test cartridge for performing tests on said biological sample, the test cartridge being provided with a computer-readable test cartridge identifier. A computer device is used to: read said computer-readable identifier from the test cartridge; receive user account information, and communicate with a server or servers via a data communication network to set-up a user account at the server(s) associated with the test cartridge identifier. The method further comprises using the wearable computer device to read the computer-readable identifier from the test cartridge; mechanically connecting the test cartridge to a test control system, whilst coupling the wearable computer device to the test control system. At the test control system, the test cartridge identifier is received from the wearable computer device and then sent to the server(s) via the communication network. The method further comprises: operating the test control system to cause the test cartridge to perform the tests on the biological sample and to obtain test results from the test cartridge and installing a database of product codes into a memory of the wearable device. The test results are sent from the test control system to the server(s) via the communication network and at the server(s), the test results are processed to generate analysis results and, using the association between the user account and the test cartridge identifier, the analysis results are associated with the user account. The method also comprises: sending the analysis results to the wearable device and installing them into the memory of the wearable computer device, the analysis results comprising information which defines a product recommendation for benefitting the health of the user, or from which such a product recommendation can be derived, for each of the product codes.

The steps of the method do not necessarily have to be carried out in the order given above. For example, the user account may be set-up either before or after operating the test control system to perform the tests on the biological sample.

Examples of a wearable device include: a ring or keyring; a standalone unit suitable for example for carrying in a purse, bag or pocket; a module for attachment to a wristband of a watch; and a module integrated into a wristband.

The product codes may correspond to machine readable codes such as 1D or 2D barcodes (e.g. UPC/EAN), QR, ISBN, PDF417, Data Matrix etc.

The analysis results may be sent to the wearable device via the test control system.

The analysis results may comprise a set of codes which identify genetic nutrition-traits of the user from which product recommendations can be derived. For example, the analysis results may comprise TPS codes associated with genotyping test results as described in WO2017/055867 (see e.g. the paragraph spanning pages 23 and 24).

Operating the test control system to cause the test cartridge to perform the tests on the biological sample may be conditional upon the server(s) determining that the test cartridge identifier is associated with a user account.

The database of product codes may be installed into the memory of the wearable device whilst the tests are being performed on the biological sample. Optionally, the wearable device may be coupled to the test control system whilst the database of product codes is installed.

The server(s) may respond to the test control system sending the test cartridge identifier by sending a test identifier to the test control system via the communication network, the test identifier being associated with the test cartridge identifier and/or user account at the server(s).

The method may further comprise at the server(s), using the test identifier to associate the received test results and/or analysis results with the test cartridge identifier and/or user account at the server(s).

The method may comprise using the analysis results to generate product recommendations for each of a multiplicity of products having associated product codes. The method may comprise installing the product codes and respective product code recommendations into a product recommendation database of the wearable computer device. The product codes may be installed into the product recommendation database before the tests on the biological sample are completed.

The computer-readable identifier may be a one-dimensional or two-dimensional barcode and the wearable computer device and the computer device may each comprise an optical component for reading the barcode.

The biological sample of the user may be a DNA sample and the analysis results may comprise a genotype for the user.

Processing the test results to generate analysis results may require the test cartridge identifier.

The method may further comprise: generating a unique access key for the wearable computer device; and using the unique access key to protect the analysis results installed into the memory of the wearable computer device, wherein access to the analysis results requires the unique access key.

The unique access key may comprise a unique customer identifier and a passcode, such as a password.

The user account information may comprise information for contacting the user, such as an email address or a telephone number.

The method may comprise using the user account information to send an activation code to the user, wherein the unique access key allows a personal computing device of the user to retrieve the unique access key.

The wearable device may be a wrist-worn wearable device or smartphone. The computer device may be a tablet computer device. The test control system may be a desktop system.

According to a further aspect of the invention there is provided a method of operating a user computer device in order to provide product and/or service recommendations to a user of the user computer device. The method comprises identifying products available for purchase, applying a filter to these products, and displaying the filtered results to the user via a graphical user interface of the user computer device. The filter is derived from genetic information of the user and is made available to the user computer device upon the establishment of a wired or short-range wireless digital data communication link between the user computer device and a wearable computer device.

The user computer device is a device which can be used for making online purchases, such as a desktop or laptop personal computer, a tablet, or a smartphone. It may have, for example, a user input device such as a touchscreen, keyboard and/or mouse which allows the user to select products for purchasing. In many cases, the wearable computer device may lack a graphical user interface and/or user input device which is suitable for making online purchases. The wearable computer device may be, for example, a module attachable to (or integrated into) a wristband, lanyard, keyring etc.

Although the term "product" may include tangible products such as groceries, beverages, and cosmetics etc, it may also encompass "intangible" products, such as services. The products may be filtered in many different ways. For example, the products may be ranked, with only a certain number of the top-ranking products being included in the filtered results. Alternatively (or additionally) the filter may apply a criterion based on the user's genetic information to each of the products, e.g. a criterion based on a maximum amount of a particular ingredient or type of ingredient, such as sugars or fats, which is acceptable for the user based on their genotype. In some cases, the filtering is based on genetic filter codes mapping to respective products or services or categories of products or services (but which may not explicitly identify a user's biological information). In general, the genetic information is determined by genotyping (e.g. SNP genotyping) a biological sample provided by the user.

The filter may be made available to the user computer device directly from the wearable computer device, e.g. the filter is transferred from the wearable computer device to the user computer device using the wired or short-range wireless digital data communication link. Alternatively, the wearable computer device may transfer an access key to the user computer device, which allows the user computer device to download the filter from a server. Optionally, the access key may be valid for only a predefined period, so that the user computer device has access to the filter for only a limited time. The access key may, for example, be generated by the wearable computer device for "one time" use by the user computer device.

The graphical user interface may display the filtered results by, for example: graphically de-emphasising or "graying out" unsuitable products; providing a graphical indication of each product's suitability (such as a tick or cross), or using colours such as red, green and amber in a "traffic light" system for indicating product suitability. Some or all the products may also be displayed in an order based on their suitability for the user. In some cases, unsuitable products may be displayed on the graphical user interface without being selectable by the user for purchase. Alternatively a message or warning may be displayed to the user if he or she selects an unsuitable product. Optionally, the message or warning comprises a suggestion of an alternative (similar) product which is more suitable.

The graphical user interface may be provided by an application or a web browser installed on the user computer device. A plug-in may be installed on the user computer device which modifies the output of the web browser in order to display the filtered results to the user.

In some implementations, the wired digital data communication link is a USB or micro USB connection. The short-range wireless digital data communication link may generally have a range of less than 1 m and may be a near-field communication (NFC) link, although other short-range wireless communication protocols can also be used.

According to a still further aspect of the invention there is provided a method of setting up a wearable user device to allow a user to scan products and obtain product recommendations based on the user's personal biological/genetic data. The method uses a cartridge to perform a test on the user's personal biological/genetic data in conjunction with a desktop test control system into which the cartridge is plugged. A user account is first created using a tablet computer or the like and which communicates with an account server. The account is associated with a cartridge ID that is read from the cartridge by the tablet. The cartridge ID is also read using the wearable user device and passed via the test control system to the server when the wearable user device is coupled to the test control system. This allows the test to be associated with the already established user account. The test control system communicates test results to the server which analyses the test results to generate analysis results. The analysis results are then downloaded to the wearable user device via the test control system or via some other channel. Product codes are also downloaded to the wearable user device, and stored in association with the product codes.

DETAILED DESCRIPTION

The present invention addresses the problems discussed above by providing a process and system which allows sensitive biological tests to be carried out outside of a laboratory environment whilst maintaining user privacy and confidence. A test kit ("cartridge") with a unique identifier in the form of a machine readable code is used to coordinate the testing process. The unique identifier can be read from the test kit using a computer device, such as a tablet, which is also used to receive the user's consent, e.g. by the user accepting an agreement or signing a digital document. The unique identifier can then be associated with the user to indicate that the user has consented to the test. In some cases, initiating the test may require that the unique identifier has been associated with the user. A user's wearable device, which has an in-built code reader for reading product codes, is also used to read the identifier. This avoids the identifier from having to be read by the testing system itself (or being input manually), which makes the testing system simpler to construct and to operate. It also allows the wearable device to be used to control when the identifier is provided to the testing system to initiate the test, thereby avoiding a test being performed without the user's wearable device.

By way of example only, the following embodiment relates to a service according to which a service provider enables users, i.e. customers or clients, to scan barcodes on food and drink products available for purchase, using wearable devices, and receive immediate product recommendations based upon users' personal genetic traits and product contents. Clearly however, it will be appreciated that the invention can be applied in other areas and to other product types such as cosmetics, cosmeceuticals, nutraceuticals, and medicines.

Figure 1:
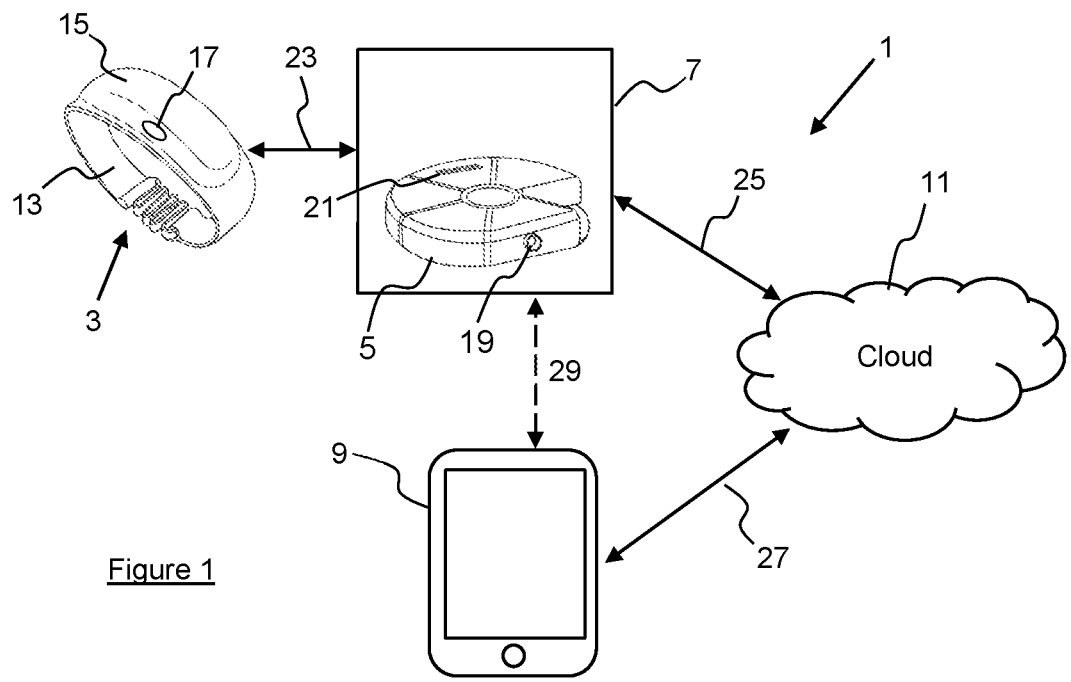
FIG. 1 is a schematic view of a system for performing a biological test and transferring an analysis of the test results to a wearable device.

FIG. 1 illustrates schematically a system 1 which is used to provide food and drink product recommendations, which are personalised according to the user's personal genetics, to a user's wearable device 3. The system 1 comprises a cartridge 5 for use in genotyping a sample provided by the user, an SNP genotyping device 7, an operator device 9 and one or more servers 11 implemented, for example, as part of a "cloud" computing environment.

The exemplary wearable device 3 shown in FIG. 1 comprises a wristband 13 and a module or "capsule" 15 which is inserted into a pocket of the wristband 13 so that it can be worn on a user's wrist. In very general terms, the capsule 15 is constructed and configured to maintain data relating to current products including product codes and respective product recommendations determined using personalised genetic data, preferably (though not necessarily) of the wearer. These product codes correspond to machine readable codes such as 1D or 2D barcodes (e.g. UPC/EAN), QR, ISBN, PDF417, Data Matrix etc, etc. The capsule 15 is provided with a code reader 17 such as a barcode reader for reading product codes printed or otherwise provided on products intended for purchase or use. One such example of a product code reader is a camera, with associated processing circuitry for recognising an imaged barcode and for converting the barcode into a digital code.

The cartridge 5 comprises an inlet port 19 into which a buccal swab can be inserted in order to provide a sample of a user's DNA for genotyping. The cartridge 5 comprises a chip module (not shown) which is configured to perform amplification and sequencing of the DNA. By way of example, the chip may use an ISFET-based detection system such as that developed by DNAe™, London, UK. The chip module comprises various components including filled reagent chambers, microfluidics, a heater or heaters, and control electronics. Reagents and buffers are also held in other parts of the cartridge. Another example uses fluorescence imaging to determine the SNPs present in the amplified DNA sample. Regardless of which detection method is used, a barcode (or other machine readable code) 21 is provided on the exterior of the cartridge 5 (or is otherwise made visible, e.g. through a transparent wall of the cartridge) to provide a unique identifier for the cartridge 5, which can be read using the code reader of the capsule 15 and using a code reader (not shown) on the operator device 9.

The operator device 9 shown in FIG. 1 is a portable computing device, such as a tablet computer, which allows user data to be entered into it conveniently, e.g. through a touch screen interface. Other forms of computing device, such as a smart phone, laptop computer or computer terminal can of course also be used, but it is generally preferable to use a portable computing device as this provides greater flexibility. For example, a portable operator device can allow an operator and a user to move to a more private location to discuss the test which is going to be performed.

The wearable device 3 communicates with the genotyping device 7 through a wired connection 23, such as a Pogo pin, although of course other forms of connection may be used, such as wireless connections via Bluetooth™, WiFi and the like. The genotyping device 7 and the operator device 9 each communicates with a server 11 through a respective wired or wireless connection 25, 27, preferably using HTTPS for secure communication over the internet or another suitable network. The operator device 9 may also have a connection 29 to the genotyping system 7, which allows the test to be controlled, and progress monitored, using the operator device 9, e.g. via Bluetooth.

The system 1 may be wholly or partially located in a user-accessible environment, such as a retail environment. Typically, but not always, the genotyping system 7 will be located in a shop or shopping centre and one or more servers 11 will be located at a remote, secure location. Providing the genotyping system 7 in a retail environment allows a test to be performed immediately after the user has provided their consent and biological sample. This helps avoid delay, such as transferring the sample to a remote facility, and also allows users the chance to oversee the testing process to alleviate concerns over the privacy and security of the test.

Generally speaking, a customer may purchase the wearable device 3 and testing cartridge 7 together and then ask the operator working in the retail environment for assistance in performing the genotyping test. As already noted above, customer privacy is of critical importance when it comes to offering personalised genetic-based services, not only because of the real threat of data leaking to unscrupulous parties, but also because of the need to ensure that users trust the services and are therefore willing to make use of them. In particular, it is very important that the user consents to the genotyping operation being performed and that a record of the consent is retained. Indeed, in some cases, it may be a legal requirement that proof of the user's consent to testing is retained for a certain period.

The operator helps the customer to enter required user information (such as name, date-of-birth, country-of-interest for the product recommendations, etc.) into the operator tablet 9. [The user may also provide lifestyle/phenotype information if this is useful in deriving product recommendations although such use is not described here.] A user interface is provided which the customer can use to signal his or her consent to the genetic test being performed. The operator uses the camera of the tablet device 9 to capture the barcode ("unique identifier") 21 on the cartridge 5 in order to link the user's information and consent to the cartridge 5. The operator may also enter the customer's mobile telephone number, email address etc., so that that an activation code can later be sent to a user's computer device, as described below with reference to FIG. 2. Once these steps are completed, the information provided by the user is sent to a server 11 via "connection" 27. The server 11 then creates a user account with a record of the unique identifier for the testing cartridge 5 for which the customer has provided his or her consent. Alternatively, if the server 11 already has an account for the user, e.g. because the user has decided to perform another test with biomarkers for different traits, then the identifier may be associated with a pre-existing user account.

To prepare for the test, the operator assists the customer in carrying out a cheek swab and inserts the swab into the cartridge 5 through the inlet port 19. The operator (or customer) uses the capsule 15 of the wearable device 3 to read the barcode 21 on the cartridge 5. The capsule 15 is then connected to the genotyping system 7 through the connection 23 and the cartridge 5 is inserted into or "docked" with the genotyping system 7 so that the test can be performed. The connection 23 between the capsule 15 and the genotyping system 7 may, in some cases, also be used to charge a power source (not shown), such as a battery, for the capsule 15.

The test may be initiated by the operator pressing a button (not shown) on the capsule 15, which causes the capsule 15 to send the previously read unique cartridge identifier to the genotyping system 7 via its wired connection 23. The genotyping system then sends a request to the server 11 to start a new test using connection 25. The request contains the cartridge unique identifier so that the server 11 can link the genetic test which is being performed with the user account, and hence with the user consent obtained already using the tablet device 9. The initiation of the test may be conditional on the server 11 determining that consent has been obtained in order to prevent unauthorised tests from being performed. In other cases, the server 11 may allow the test to be initiated but only process the test data or release the test results once the user's consent has been obtained.

The genotyping system 7 generates test results based on which of a set of SNPs are present in the user's DNA. The test results may, for example, comprise electrochemical measurements or fluorescence images of an array of test sites loaded with different biomarkers on the cartridge 5. Typically, the genotyping system 7 does not have the information and/or the processing power necessary to analyse the test results to identify the user's genotype. For example, the identities of the biomarkers stored in the cartridge 5 may be stored only at the server 11, so that it is not possible to interpret the raw test results without the involvement of the server 11 (again, this is a feature that provides increased user privacy). The genotyping system 7 therefore sends the test results to the server 11 for processing.

The server 11 performs an analysis of the test results to determine which of the SNPs probed by the test cartridge 5 are present in the user's DNA, i.e. a genotype result for the user. Based on this information the server then identifies values for certain nutrition related traits, e.g. caffeine metabolism, calorie sensitivity, carbohydrate sensitivity, etc. The server 11 also generates personalised product recommendations based on these trait values and the contents of known products maintained in a product database The results of the analysis are then downloaded to the capsule 15 from the server 11 via the genotyping system 7. The results may be downloaded step-wise as the test progresses, i.e. as the test results become available at the server 11, or after the testing is complete. The end of the test may be signalled to the operator using some form of indicator, such as an LED or audible alarm (not shown) provided on the capsule 15, and/or using the tablet 9.

A database of product codes and product recommendations are also transferred to the capsule 15 from the server 11 during and/or after the test. The use of the wired connection 23 allows this transfer to be effected rapidly. Moreover, and importantly, it avoids the need for any wireless pairing to be performed with the capsule at the test location, an operation that can often be slow and problematic. When the customer subsequently uses the capsule 15 to read a product code from a product, the database is used by the capsule 15 to look-up the relevant product recommendation. The capsule 15 then provides the recommendation as to whether or not the product is suitable for the user. The product codes may be sent to the capsule 15 at a different time from the product recommendations. For example, the product codes may be transferred to the capsule 15 from the server 11 during the running of the test, with the product recommendations being transferred sometime after the test has been completed, e.g. after the user has returned home with the capsule 15. This allows the capsule 15 to be removed from the genotyping system 7 before the testing process is completed.

Several different approaches may be used to provide product recommendations which are personalised according to genotype. As mentioned above, each product may have an associated product recommendation as determined from the results of the SNP genotyping, which has the advantage that the product recommendation can be provided simply by looking up the relevant product in the database. Alternatively, a multi-step process can be used in which each product is not directly associated with a recommendation. Instead, a database of product information may be provided, from which information about the composition of the product can be obtained using the product code. This compositional information may include, for example, details of the sugar or fat content of the product, as well as whether it contains potential allergens such as nuts or gluten, for example. The capsule 15 may then store a collection of genetically-derived "scores" against which the composition of the product can be compared in order to derive a product recommendation. For example, a product may have a cholesterol content which exceeds a threshold set by the user's score for cholesterol, in which case the product would not be recommended for the user. This latter approach has the advantage that the product information and/or scores can be updated independently of one another, e.g. when a product changes, Before it is connected to the genotyping system 7, the capsule 15 may be pre-configured with only minimal operating software or software which has been superseded by a more recent version. The server 11 may therefore provide new or updated software to the capsule 15, before, during and/or after the test, taking advantage of the bandwidth, speed and reliability of the wired connection 23 to the genotyping system 7 to carry out the data transfer.

The server 11 also sends, via the genotyping system 7, a capsule access key to the capsule 15, which the capsule 15 uses to protect some or all of the data it has downloaded. The capsule access key can, for example, comprise a unique customer identifier and passcode (e.g. a password) which must both be provided to connect to the capsule 15. Other types of device which are able to connect to the capsule 15 are unable to access the personal information which is stored on it without providing the access key (see below).

On completion of the test, the operator or customer removes the capsule 15 from the genotyping system 7 and inserts it into the wristband 13. As the personalised data has been loaded onto the capsule 15, the customer may immediately begin to use the wearable device 3 to obtain personalised product recommendations. The capsule 15 generally comprises a signalling device to communicate the product recommendation to the customer after he or she has used the capsule 15 to read a product code from a product. For example, the capsule 15 may use an LED which changes colour according to the product recommendation, e.g. green or red depending on whether the product is or is not recommended for the user. In general, no further setup of the capsule 15 is required before it can used, e.g. it is not necessary for the customer to connect another computer device, such as their smartphone, to the capsule 15 to configure it. The customer may therefore immediately re-insert the capsule 15 into the wristband 13 and use the wearable device 3 to obtain personalised product recommendations. This greatly improves the customer experience as the time taken from initial purchase to first product scan can be a matter of minutes. Upon completion of the test, the server 11 sends a message containing an activation code, e.g. a 4-digit numerical PIN code, to the customer using the previously provided contact information, typically in the form of an SMS message or email.

Figure 2:
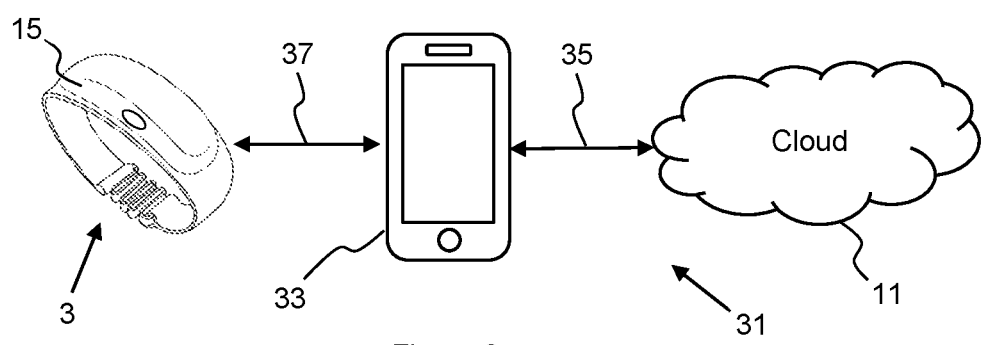
FIG. 2 is a schematic view of a system for securely accessing the analysis from the wearable device of FIG. 1.

FIG. 2 illustrates schematically a system 31 which allows the customer to use a smartphone 33, or other personal computing device such as a tablet or smartwatch, to access the data stored on the capsule 15. This procedure is typically carried out after the user has purchased the wristband/capsule and the test has been completed, e.g. when the user has returned home. The customer uses an internet connection 35 of his or her smartphone 33 to download software (e.g. an app) for accessing and interacting with/updating the data stored on the capsule 15. The app can be downloaded from the server 11 or another content distribution platform such as an "app store". The smartphone will have previously received the activation code from the server 11. When the app is first opened, it prompts the user to enter the activation code. The app then sends a request to the server 11 which includes the activation code and the server 11 responds with the capsule access key, which is saved by the smartphone 33. The user or the app then initiates Bluetooth pairing with the capsule 15. During or following pairing the app provides the capsule access key to the capsule. The capsule 15 then authenticates the user by comparing the received capsule access key with its own stored copy of the capsule access key. If the keys match, a connection 37 is established which allows the capsule 15 and the app to interact. The capsule access key may be exchanged each time communication between the app and the capsule is initiated, or some alternative authentication mechanism may be established which does not use the capsule access key.

This approach for allowing secure access avoids the need for any complicated (e.g. Bluetooth) setup at the time the test is performed and frees the customer from the burden of having to manage the security of the capsule 15 themselves, e.g. by setting up or remembering a password.

As described above, the capsule 15 may be used to provide product recommendations to the user whilst he or she is shopping, by using a product code reader built into the capsule 15. However, the capsule 15 may also be used to facilitate product or service purchases which are conducted online, e.g. using a web browser with the plug-in described in WO2017/055867 (see page 19, final paragraph) installed on a personal computer device such a home computer, tablet or smartphone. For example, the plug-in may be used to de-emphasise or "gray out" products which are not recommended for the user based on their genotype.

The capsule 15 is connected to the personal computer device using a wired (e.g. USB) or short-range (e.g. NFC) wireless connection. The personal computer device may be configured to load or activate the browser plug-in (or other online shopping software) in response to detecting that such a connection to the capsule 15 has been established. Similarly, the browser plug-in may be unloaded or deactivated once the capsule 15 is disconnected from the personal computer device. This provides the user with a convenient way of initiating the online shopping session.

In many cases, the capsule 15 acts as a "key" for unlocking the user's genetic information so that personalised product recommendations can be provided during online shopping. Requiring the capsule 15 to be physically present whilst the user is shopping online helps to reassure the user that their personal genetic data is being handled securely and also helps reinforce their feeling of "ownership" or personal "connection" to their data The capsule 15 may store or generate an access key which can be used by a web browser or other application installed on the personal computer device to gain access to product recommendations (or information from which product recommendations can be derived) from the cloud. This access key is, in general, different from the capsule access key required to establish a connection between the app described above and the capsule 15. The personal computer device may be granted access on a temporary basis, e.g. for a certain time, or until the online shopping session is completed, so that the personal computer device is not able to access the product recommendations (or other information) after the capsule 15 is disconnected.

Alternatively, the personal computer device may access product recommendations (or other information personal to the user) directly from the capsule 15, thereby avoiding the need to transfer the user's generically derived data across the internet. In another implementation, the browser plug-in may configure the web browser to use a proxy server through which communications between the personal computer device and an online shopping web site are routed. For example, a list of products sent from the shopping web site to the browser may be intercepted at the proxy server and the list of products filtered based on product recommendations stored at the proxy server.

According to a further alternative approach, the personal computer may obtain from the connected capsule a set of codes which identify genetic nutrition-traits of the user and which can be used to filter products viewed online (or may be granted permission by the capsule to obtain these codes via the Internet). These codes might, for example, identify the user's sensitivity to certain substances such as caffeine, sugar, carbohydrates, etc.

Figure 3:
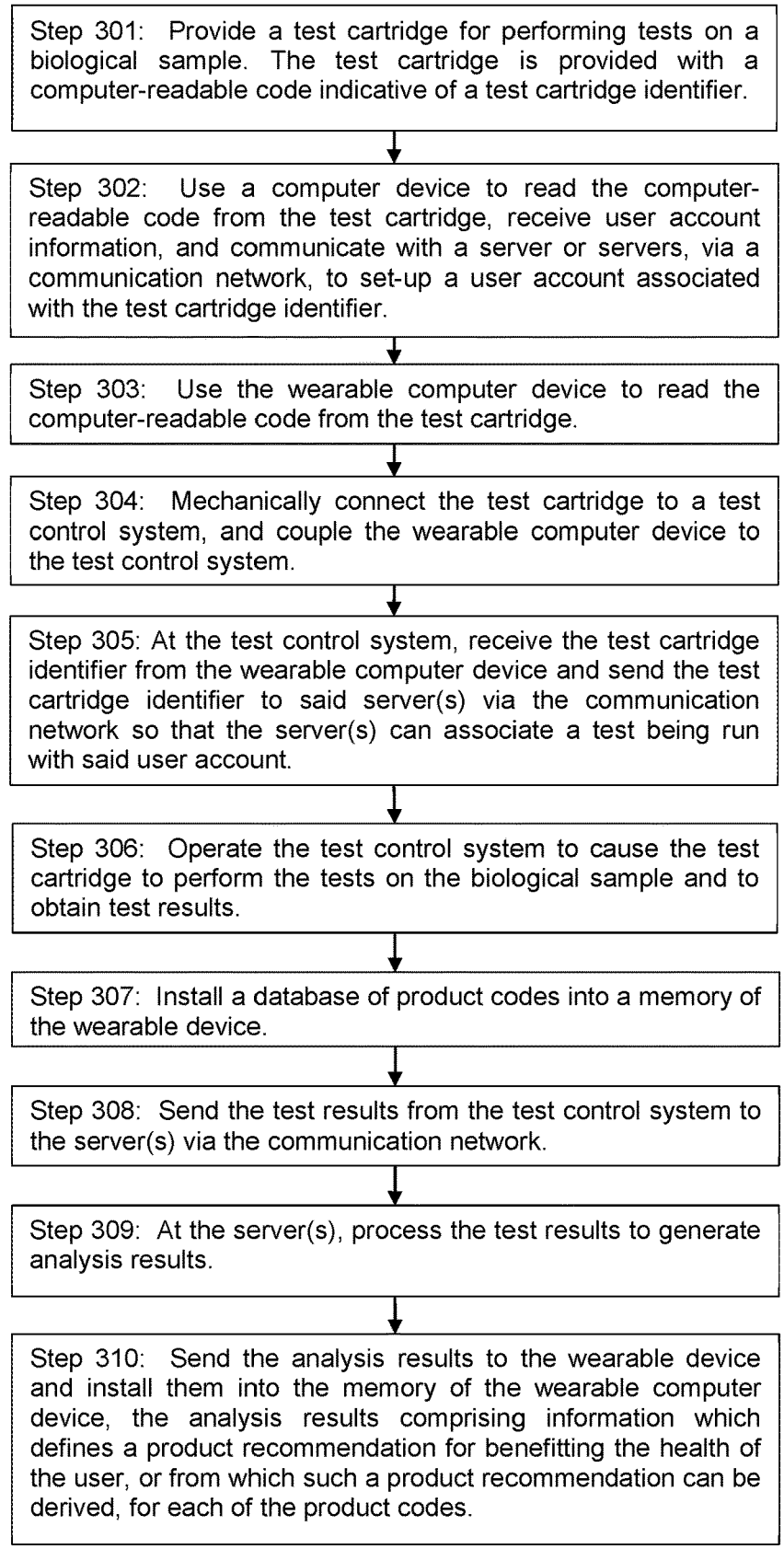
FIG. 3 is a flow diagram of a method of performing a biological test and transferring an analysis of the test results to a wearable device.

FIG. 3 is an overview of the method described in connection with FIG. 1. The method comprises the following steps:

Step 301: Provide a test cartridge for performing tests on a biological sample. The test cartridge is provided with a printed computer-readable code indicative of a test cartridge identifier.

Step 302: Use a computer device to read the computer-readable code from the test cartridge, receive user account information, and communicate with a server or servers, via a communication network, to set-up a user account associated with the test cartridge identifier.

Step 303: Use the wearable computer device to read the computer-readable code from the test cartridge;

Step 304: Mechanically connect the test cartridge to a test control system, and couple the wearable computer device to the test control system.

Step 305: At the test control system, receive the test cartridge identifier from the wearable computer device and send the test cartridge identifier to the server(s) via the communication network so that the server(s) can associate a test being run with said user account.

Step 306: Operate the test control system to cause the test cartridge to perform the tests on the biological sample and to obtain test results.

Step 307: Install a database of product codes into a memory of the wearable device.

Step 308: Send the test results from the test control system to the server(s) via the communication network.

Step 309: At the server(s), process the test results to generate analysis results. Use the test cartridge identifier received from the test control system to associate the analysis results with the user account.

Step 310: Send the analysis results to the wearable device and install them into the memory of the wearable computer device, the analysis results comprising information which defines a product recommendation for benefitting the health of the user, or from which such a product recommendation can be derived, for each of the product codes.

Figure 4:
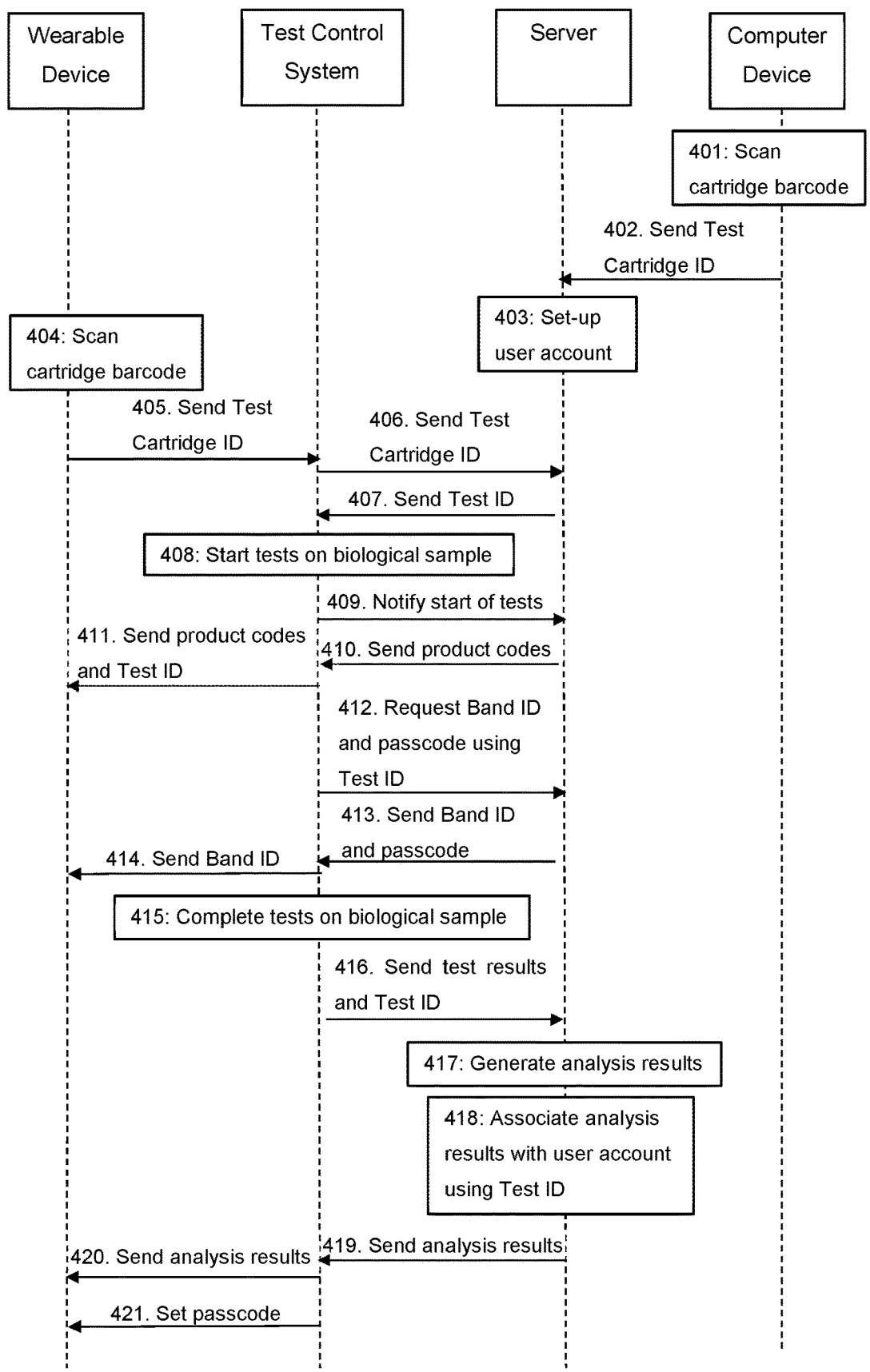
FIG. 4 is a sequence diagram of a method of performing a biological test and transferring an analysis of the test results to a wearable device.

FIG. 4 illustrates an exemplary sequence of events occurring during a method as described above in relation to FIG. 1. These include:

Step 401: The computer device (e.g. operator tablet 9) scans the test cartridge barcode to obtain the test cartridge identifier.

Step 402: The computer device sends the test cartridge identifier to the server (or servers).

Step 403: The server sets up a user account using the test cartridge identifier.

Step 404: The wearable device (e.g. capsule 15) scans the test cartridge barcode to obtain the Test Cartridge ID.

Step 405: The wearable computer device sends the test cartridge identifier to the test control system.

Step 406: The test control system sends the Test Cartridge ID to the server.

Step 407: The server responds to the test control system by sending a Test ID.

Step 408: The test control system starts to perform tests on the biological sample, e.g. tests to identify particular SNPs that the user has. To start the tests, an operator may, for example, press a button on the wearable device to cause the wearable device to send a signal to the test control system to initiate the tests. The tests can be performed in parallel while further steps are performed.

Step 409: The test control system notifies the server that tests have started.

Step 410: The server sends product codes to the test control system.

Step 411: The test control system forwards the product codes and Test ID to the wearable device.

Step 412: The test control system sends the Test ID to the server to request a Band ID and passcode.

Step 413: The server responds to the request by sending a Band ID and passcode to the test control system.

Step 414: The wearable device receives the Band ID from the test control system and stores it.

Step 415: The test control system completes the tests on the biological sample.

Step 416: The test control system sends the test results and the Test ID to the server (either together or separately, in any order).

Step 417: The server generates analysis results using the received test results.

Step 418: The server uses the Test ID to associate the analysis results with the user account.

Step 419: The server sends the analysis results to the test control system.

Step 420: The test control system forwards the analysis results to the wearable device.

Step 421: The test control system sets the passcode on the wearable device. It may be preferable to set the passcode after the analysis results have been transferred to the wearable device to avoid the need for the test control system to use the password to connect to the device.

The initial setup of the wearable device (steps 404 to 414) may typically be completed in a matter of minutes, whereas the testing and analysis steps (steps 415 to 418) may take longer, perhaps of the order of 40 minutes. However, after step 414 has been completed, the wearable device can optionally be disconnected from the test control system whilst the testing and analysis are completed. The analysis results can then be downloaded to the wearable device subsequently using, for example, the user's smartphone via an internet connection to the server. As well as the analysis results, the smartphone (or other user device) can also receive the passcode from the server and use it to set the passcode on the wearable device. Optionally, the user may be prompted to retrieve the analysis results by sending him or her a message (such as an SMS message or email message) using information provided for setting up the user account. Preferably, the message is sent after the analysis results have been associated with the user account (step 418).

Although steps 416 and 418 refer to the Test ID being sent to the server, to allow the server to associate the analysis results with the user account, alternatively the Test Cartridge ID can be used for this purpose. Optionally, the test results themselves may be associated with the user account and stored by the server, which may, for example, allow the analysis to be repeated with a different algorithm at a later time.

The progress of the method or the occurrence of any errors may be signalled to an operator using some form of indicator, such as an LED, provided on the wearable device and/or using the computer device.

It will be appreciated by the person of skill in the art that various modifications may be made to the above described embodiments without departing from the scope of the invention. For example, although the description has focussed on genotyping, the invention may be applied to other forms of biological sample analysis such as breath testing or the test may involve analysing the user's microbiome.

The invention claimed is:

1. A method of obtaining and installing, into a memory of a wearable computer device, analysis results for a biological sample of a user, the method comprising:

providing a test cartridge for performing tests on said biological sample, the test cartridge being provided with a computer-readable test cartridge identifier;

using a computer device other than the wearable computer device to:

read, from the test cartridge, said computer-readable identifier;

receive user account information; and communicate with a server or servers via a data communication network to set-up, at said server or servers, a user account associated with said test cartridge identifier;

using the wearable computer device to read, from the test cartridge, the computer-readable identifier;

mechanically connecting the test cartridge to a test control system, and coupling the wearable computer device to the test control system;

at the test control system, receiving, from the wearable computer device, the test cartridge identifier and sending it to said server or servers via said communication network, wherein the server or servers use said cartridge identifier to associate a test being run with said user account;

operating the test control system to cause the test cartridge to perform said tests on the biological sample in order to obtain test results;

sending the test results from the test control system to said server or servers via said communication network;

at the server or servers, processing the test results to generate analysis results; and sending the analysis results to the wearable device and installing them into said memory of the wearable computer device, the analysis results comprising information which defines a product recommendation for benefitting the health of the user, or from which such a product recommendation can be derived, for each of a multiplicity of product codes, the method further comprising installing a database containing said product codes into a memory of the wearable device either before, during or upon completion of said test.

2. A method according to claim 1, wherein the analysis results are sent to the wearable device via the test control system.

3. A method according to claim 1, wherein the analysis results comprise a set of codes which identify genetic nutrition-traits of the user from which product recommendations can be derived.

4. A method according to claim 1, wherein operating the test control system to cause the test cartridge to perform said tests on the biological sample is conditional upon said server or servers determining that the test cartridge identifier is associated with a user account.

5. A method according to claim 1, wherein the database of product codes is installed into the memory of the wearable device whilst said tests are being performed on the biological sample and/or wherein the wearable device is coupled to the test control system whilst the database of product codes is installed.

6. A method according to claim 1, wherein the server or servers responds to the test control system sending the test cartridge identifier by sending a test identifier to the test control system via said communication network, the test identifier being associated with the test cartridge identifier and/or user account at the server or servers.

7. A method according to claim 6, further comprising at said server or servers, using the test identifier to associate the received test results and/or the analysis results with said test cartridge identifier and/or user account at the server or servers.

8. A method according to claim 1 and comprising using the analysis results to generate product recommendations for each of a multiplicity of products having associated product codes.

9. A method according to claim 8 and comprising installing the product codes and respective product code recommendations into a product recommendation database of the wearable computer device.

10. A method according to claim 1, wherein the computer-readable identifier is a one-dimensional or two-dimensional barcode and the wearable computer device and the computer device each comprise an optical component for reading said barcode.

11. A method according to claim 1, wherein the biological sample of the user is a DNA sample and the analysis results comprise a genotype for the user.

12. A method according to claim 1, wherein processing the test results to generate the analysis results requires the test cartridge identifier.

13. A method according to claim 1, further comprising:
generating a unique access key for the wearable computer device; and
using the unique access key to protect the analysis results installed into said memory of the wearable computer device, wherein access to the analysis results requires the unique access key.

14. A method according to claim 13, wherein the unique access key comprises a unique customer identifier and a passcode.

15. A method according to claim 14, wherein the user account information comprises information for contacting the user.

16. A method according to claim 15 and comprising using the user account information to send an activation code to the user, wherein the unique access key allows a personal computing device of the user to retrieve the unique access key.

17. A method according to claim 1, wherein the wearable device is a wrist-worn device or is configured to fit within a wristband.

18. A method according to claim 1, wherein the wearable device is a smartphone.

19. A method according to claim 1, wherein the computer device is a tablet computer device and/or the test control system is a desktop system.

* * * * *